(12) United States Patent
Chappa et al.

(10) Patent No.: US 11,027,049 B2
(45) Date of Patent: Jun. 8, 2021

(54) DEVICES AND METHODS FOR DELIVERY OF BIOACTIVE AGENTS

(71) Applicant: Surmodics, Inc., Eden Prairie, MN (US)

(72) Inventors: Ralph A. Chappa, Ham Lake, MN (US); Andrew G. Bach, Edina, MN (US)

(73) Assignee: Surmodics, Inc., Eden Prairie, MN (US)

( * ) Notice: Subject to any disclaimer, the term of this patent is extended or adjusted under 35 U.S.C. 154(b) by 7 days.

(21) Appl. No.: 15/994,263

(22) Filed: May 31, 2018

(65) Prior Publication Data

US 2018/0272040 A1 Sep. 27, 2018

Related U.S. Application Data

(63) Continuation of application No. 12/769,127, filed on Apr. 28, 2010, now Pat. No. 10,058,634.

(60) Provisional application No. 61/173,462, filed on Apr. 28, 2009.

(51) Int. Cl.
*A61L 29/08* (2006.01)
*A61L 29/16* (2006.01)

(52) U.S. Cl.
CPC .............. *A61L 29/085* (2013.01); *A61L 29/16* (2013.01); *A61L 2300/416* (2013.01); *A61L 2300/60* (2013.01)

(58) Field of Classification Search
CPC ... A61L 29/085; A61L 29/16; A61L 2300/416
See application file for complete search history.

(56) References Cited

U.S. PATENT DOCUMENTS

| | | |
|---|---|---|
| 3,389,099 A | 6/1968 | Dressler et al. |
| 4,195,637 A | 4/1980 | Gruntzig et al. |
| 4,490,421 A | 12/1984 | Levy |
| 4,722,906 A | 2/1988 | Guire |
| 4,973,493 A | 11/1990 | Guire |
| 4,979,959 A | 12/1990 | Guire |
| 5,002,582 A | 3/1991 | Guire et al. |
| 5,041,089 A | 8/1991 | Mueller et al. |
| 5,087,246 A | 2/1992 | Smith |
| 5,201,753 A | 4/1993 | Lampropoulos et al. |
| 5,263,992 A | 11/1993 | Guire |
| 5,297,607 A | 3/1994 | Beauchamp |
| 5,318,587 A | 6/1994 | Davey |
| 5,334,146 A * | 8/1994 | Ozasa ............... A61M 25/1029 604/103.06 |
| 5,382,234 A | 1/1995 | Cornelius et al. |
| 5,414,075 A | 5/1995 | Swan et al. |
| 5,512,329 A | 4/1996 | Guire et al. |
| 5,556,383 A | 9/1996 | Wang et al. |
| 5,571,089 A | 11/1996 | Crocker |
| 5,616,608 A | 4/1997 | Kinsella et al. |
| 5,632,773 A | 5/1997 | Graham et al. |
| 5,637,460 A | 6/1997 | Swan et al. |
| 5,714,360 A | 2/1998 | Swan et al. |
| 5,741,551 A | 4/1998 | Guire et al. |
| 5,776,101 A | 7/1998 | Goy |
| 5,807,331 A | 9/1998 | Den Heijer et al. |
| 5,811,447 A | 9/1998 | Kunz et al. |
| 5,833,657 A | 11/1998 | Reinhardt et al. |
| 5,858,653 A | 1/1999 | Duran et al. |
| 5,882,336 A | 3/1999 | Janacek |
| 6,007,833 A | 12/1999 | Chudzik et al. |
| 6,077,698 A | 6/2000 | Swan et al. |
| 6,168,748 B1 | 1/2001 | Wang et al. |
| 6,177,522 B1 | 1/2001 | Brady et al. |
| 6,210,364 B1 | 4/2001 | Anderson et al. |
| 6,278,018 B1 | 8/2001 | Swan |
| 6,299,604 B1 | 10/2001 | Ragheb et al. |
| 6,328,710 B1 | 12/2001 | Wang et al. |
| 6,340,465 B1 | 1/2002 | Hsu et al. |
| 6,394,995 B1 | 5/2002 | Solar et al. |
| 6,436,440 B1 | 8/2002 | Meffert et al. |
| 6,444,324 B1 | 9/2002 | Sjoquist et al. |
| 6,465,178 B2 | 10/2002 | Chappa et al. |
| 6,482,348 B1 | 11/2002 | Wang et al. |
| 6,506,411 B2 | 1/2003 | Hunter et al. |
| 6,506,895 B2 | 1/2003 | Guire et al. |

(Continued)

FOREIGN PATENT DOCUMENTS

| | | |
|---|---|---|
| CA | 2836266 | 11/2012 |
| CA | 2760187 | 1/2018 |

(Continued)

OTHER PUBLICATIONS

"Communication Pursuant to Article 94(3) EPC," for European Patent Application No. 12723063.9 dated Jan. 16, 2019 (5 pages).

(Continued)

*Primary Examiner* — Andrew S Rosenthal

(74) *Attorney, Agent, or Firm* — Pauly, DeVries Smith & Deffner LLC

(57) ABSTRACT

Embodiments of the invention include bioactive agent eluting devices. In an embodiment the invention includes a bioactive agent delivery device including a substrate, a hydrophilic polymer disposed on the substrate, and a substantially amorphous bioactive agent disposed on the surface of the hydrophilic polymer. In an embodiment, the invention includes a method of making a bioactive agent delivery device including depositing a hydrophilic polymer on a substrate forming a hydrophilic surface and depositing a substantially amorphous bioactive agent on the hydrophilic surface. In an embodiment, the invention includes a bioactive agent-eluting catheter including a catheter shaft and an expandable balloon disposed on the catheter shaft. Other embodiments are included herein.

13 Claims, 3 Drawing Sheets

(56) References Cited

U.S. PATENT DOCUMENTS

| | | | |
|---|---|---|---|
| 6,514,734 B1 | 2/2003 | Clapper et al. |
| 6,515,009 B1 | 2/2003 | Kunz et al. |
| 6,517,515 B1 | 2/2003 | Eidenschink |
| 6,544,544 B2 | 4/2003 | Hunter et al. |
| 6,603,040 B1 | 8/2003 | Swan |
| 6,613,066 B1 | 9/2003 | Fukaya et al. |
| 6,623,504 B2 | 9/2003 | Vrba et al. |
| 6,663,662 B2 | 12/2003 | Pacetti et al. |
| 6,730,064 B2 | 5/2004 | Ragheb et al. |
| 6,762,019 B2 | 7/2004 | Swan et al. |
| 6,896,842 B1 | 5/2005 | Hamilton et al. |
| 7,138,541 B2 | 11/2006 | Swan |
| 7,163,523 B2 | 1/2007 | Devens, Jr. et al. |
| 7,309,593 B2 | 12/2007 | Ofstead et al. |
| 7,507,469 B2 | 3/2009 | Yao et al. |
| 7,696,259 B2 | 4/2010 | Hanley et al. |
| 7,731,685 B2 | 6/2010 | Schaeffer et al. |
| 7,736,689 B2 | 6/2010 | Chappa et al. |
| 7,758,892 B1 | 7/2010 | Chen et al. |
| 7,797,033 B2 | 9/2010 | D'andrea et al. |
| 7,803,149 B2 | 9/2010 | Schaeffer et al. |
| 7,807,750 B2 | 10/2010 | Taton et al. |
| 7,820,193 B2 | 10/2010 | Hunter et al. |
| 7,850,727 B2 | 12/2010 | Shanley et al. |
| 8,034,765 B2 | 10/2011 | De et al. |
| 8,039,524 B2 | 10/2011 | Ralph et al. |
| 8,158,106 B2 | 4/2012 | Guire et al. |
| 8,172,793 B2 | 5/2012 | Choules et al. |
| 8,202,530 B2 | 6/2012 | Hossainy et al. |
| 8,257,305 B2 | 9/2012 | Scheller et al. |
| 8,293,262 B2 | 10/2012 | Chen et al. |
| 8,439,868 B2 | 5/2013 | Scheller et al. |
| 8,469,943 B2 | 6/2013 | Bates et al. |
| 8,487,137 B2 | 7/2013 | Guire et al. |
| 8,513,320 B2 | 8/2013 | Rooijmans |
| 8,557,272 B2 | 10/2013 | Zhao et al. |
| 8,673,387 B2 | 3/2014 | Bates et al. |
| 8,697,112 B2 | 4/2014 | Dudnyk et al. |
| 8,809,411 B2 | 8/2014 | Rooijmans |
| 8,889,760 B2 | 11/2014 | Kurdyumov et al. |
| 8,952,103 B2 | 2/2015 | Blondel et al. |
| 9,375,517 B2 | 6/2016 | Babcock et al. |
| 9,555,119 B2 | 1/2017 | Ventura et al. |
| 9,757,497 B2 | 9/2017 | Slager |
| 9,861,727 B2 | 1/2018 | Slager et al. |
| 9,999,675 B2 | 6/2018 | Ventura et al. |
| 10,058,634 B2 | 8/2018 | Chappa et al. |
| 10,213,528 B2 | 2/2019 | Slager et al. |
| 10,213,529 B2 | 2/2019 | Slager |
| 10,617,793 B2 | 4/2020 | Slager et al. |
| 2002/0006493 A1 | 1/2002 | Chabrecek et al. |
| 2002/0123801 A1 | 9/2002 | Pacetti et al. |
| 2004/0044404 A1 | 3/2004 | Stucke et al. |
| 2004/0105839 A1 | 6/2004 | Park |
| 2004/0117007 A1* | 6/2004 | Whitbourne ............ A61L 15/62 |
| | | | 623/1.42 |
| 2005/0100580 A1 | 5/2005 | Osborne et al. |
| 2005/0281857 A1* | 12/2005 | Heyer ................. A61L 33/0029 |
| | | | 424/423 |
| 2006/0020243 A1 | 1/2006 | Speck et al. |
| 2006/0030669 A1 | 2/2006 | Taton et al. |
| 2006/0148982 A1 | 7/2006 | Uchegbu et al. |
| 2007/0032882 A1 | 2/2007 | Lodhi et al. |
| 2008/0020013 A1 | 1/2008 | Reyes et al. |
| 2008/0233183 A1 | 9/2008 | Mccook et al. |
| 2009/0043378 A1 | 2/2009 | Cheng et al. |
| 2009/0221767 A1 | 9/2009 | Malet |
| 2009/0226501 A1 | 9/2009 | Parsonage et al. |
| 2009/0227946 A1 | 9/2009 | Kangas |
| 2010/0040766 A1 | 2/2010 | Chappa et al. |
| 2010/0087783 A1 | 4/2010 | Weber et al. |
| 2010/0096320 A1 | 4/2010 | Opperman et al. |
| 2010/0130837 A1 | 5/2010 | Matott |
| 2010/0272774 A1 | 10/2010 | Chappa |
| 2011/0022027 A1 | 1/2011 | Morishita et al. |
| 2011/0144373 A1 | 6/2011 | Swan et al. |
| 2011/0245367 A1 | 10/2011 | Kurdyumov et al. |
| 2011/0250255 A1 | 10/2011 | Parsonage et al. |
| 2011/0257339 A1 | 10/2011 | Fischer et al. |
| 2012/0039983 A1 | 2/2012 | Uhrich et al. |
| 2012/0046384 A2 | 2/2012 | Kurdyumov et al. |
| 2012/0083734 A1 | 4/2012 | Ayres et al. |
| 2012/0148852 A1 | 6/2012 | Jelle et al. |
| 2012/0177742 A1 | 7/2012 | Mcclain et al. |
| 2012/0177910 A1 | 7/2012 | Weber et al. |
| 2012/0296274 A1 | 11/2012 | Slager |
| 2013/0143056 A1 | 6/2013 | Swan et al. |
| 2013/0190689 A1 | 7/2013 | Slager |
| 2013/0302529 A1 | 11/2013 | Kurdyumov |
| 2014/0162083 A1 | 6/2014 | Kurdyumov et al. |
| 2014/0193474 A1 | 7/2014 | Babcock et al. |
| 2014/0276636 A1 | 9/2014 | Lee et al. |
| 2014/0336571 A1 | 11/2014 | Slager |
| 2015/0140107 A1 | 5/2015 | Slager et al. |
| 2015/0283092 A1 | 10/2015 | Ruddy et al. |
| 2017/0072057 A1 | 3/2017 | Ventura et al. |
| 2017/0112973 A1 | 4/2017 | Slager et al. |
| 2018/0110903 A1 | 4/2018 | Slager et al. |
| 2018/0169032 A1 | 6/2018 | Kloke |
| 2020/0237971 A1 | 7/2020 | Slager et al. |

FOREIGN PATENT DOCUMENTS

| | | | |
|---|---|---|---|
| CN | 1413118 | 4/2003 | |
| CN | 1950114 | 4/2007 | |
| CN | 1964750 | 5/2007 | |
| CN | 103906505 | 7/2014 | |
| EP | 0882461 | 12/1998 | |
| EP | 1176993 | 6/2003 | |
| EP | 1997525 | 12/2008 | |
| EP | 2098230 | 6/2012 | |
| EP | 2292225 | 6/2012 | |
| JP | 2009502243 | 1/2009 | |
| JP | 2014515348 | 6/2014 | |
| WO | 9964086 | 12/1999 | |
| WO | WO-9964086 A1 * | 12/1999 | ............ A61L 27/34 |
| WO | 0110468 | 2/2001 | |
| WO | 2001045742 | 6/2001 | |
| WO | 2004017943 | 5/2004 | |
| WO | 2005079754 | 9/2005 | |
| WO | 2005113034 | 12/2005 | |
| WO | 2006019848 | 2/2006 | |
| WO | 2006026187 | 3/2006 | |
| WO | 2006053175 | 5/2006 | |
| WO | 2007012051 | 1/2007 | |
| WO | 2007106441 | 9/2007 | |
| WO | 2007136504 | 11/2007 | |
| WO | 2009051614 | 4/2009 | |
| WO | 2009121629 | 10/2009 | |
| WO | 2010111517 | 9/2010 | |
| WO | 2010129328 | 11/2010 | |
| WO | 2011005421 | 1/2011 | |
| WO | 2011024831 | 3/2011 | |
| WO | 2011052089 | 5/2011 | |
| WO | 2012162061 | 11/2012 | |
| WO | 2013169879 | 11/2013 | |
| WO | 2014186729 | 11/2014 | |
| WO | 2016123480 | 8/2016 | |
| WO | 2018118671 | 6/2018 | |

OTHER PUBLICATIONS

"Communication Pursuant to Article 94(3) EPC," for European Patent Application No. 16703247.3 dated Apr. 23, 2019 (5 pages).

"Final Office Action," for U.S. Appl. No. 14/280,170 dated Apr. 5, 2019 (38 pages).

"Non-Final Office Action," for U.S. Appl. No. 15/840,540 dated Mar. 15, 2019 (15 pages).

"Non-Final Office Action," for U.S. Appl. No. 15/850,010 dated Feb. 26, 2019 (13 pages).

"Office Action," for Israeli Patent Application No. 242545 dated May 28, 2019 (8 pages) with English Translation.

(56) References Cited

OTHER PUBLICATIONS

"Response to Final Office Action," for U.S. Appl. No. 15/850,010 filed Jan. 24, 2019 (10 pages).
"Response to Final Rejection," dated Mar. 15, 2019 for U.S. Appl. No. 15/840,540, filed May 15, 2019, 13 pages.
"Response to First Examination Report," for Indian Patent Application No. 3723/KOLNP/2013 filed Feb. 20, 2019 (23 pages).
"Response to Office Action," for Canadian Patent Application No. 2,836,266 filed May 29, 2019 (19 pages).
Avella, "Addition of glycerol plasticizer to seaweeds derived alginates: Influences of microstructure on chemical-physical properties," Carbohydrate Polymers vol. 69, Issue 3, Jun. 25, 2007, 503-511.
"Communication Pursuant to Article 94(3) EPC," for European Application No. 10716714, dated Feb. 13, 2015 (6 pages).
"Communication Pursuant to Article 94(3) EPC," for European Application No. 10716714, dated Jan. 18, 2013 (5 pages).
"Communication Pursuant to Article 94(3) EPC," for European Application No. 13792207.6, dated Sep. 29, 2017 (5 pages).
"Communication Pursuant to Article 94(3) EPC," for European Patent Application No. 12723063.9 dated Jun. 12, 2017 (5 pages).
"Communication Pursuant to Article 94(3) EPC," for European Patent Application No. 14730381.2 dated Nov. 21, 2017 (4 pages).
"Decision of Refusal," for Japanese Patent Application No. 2012-508637, dated Feb. 3, 2015 (3 pages) with English summary.
"File History," for related U.S. Appl. No. 12/769,127, filed Apr. 28, 2010 to May 25, 2018 (574 pages).
"File History," for related U.S. Appl. No. 13/469,844, filed Mar. 30, 2016 to Dec. 15, 2016 (127 pages).
"File History," for related U.S. Appl. No. 13/469,844, filed May 11, 2012 to Feb. 24, 2015, 279 pages.
"File History," for related U.S. Appl. No. 13/793,390, filed Mar. 11, 2013 to Jul. 6, 2015 (157 pages).
"File History," for related U.S. Appl. No. 13/793,390, filed Nov. 16, 2015 to Dec. 19, 2016 (180 pages).
"File History," for related U.S. Appl. No. 14/072,520, filed May 13, 2015 to Jan. 12, 2017 (132 pages).
"File History," for related A U.S. Appl. No. 14/072,520, filed Nov. 5, 2013 to Feb. 18, 2015, 102 pages.
"File History," for related U.S. Appl. No. 14/280,170, filed Sep. 24, 2015 to Jan. 23, 2017 (160 pages).
"File History," for related U.S. Appl. No. 14/280,170, filed May 16, 2014 to May 13, 2015 (145 pages).
"File History," for related U.S. Appl. No. 14/609,270, filed Jan. 29, 2015 to Aug. 3, 2015 (245 pages).
"Final Office Action," for U.S. Appl. No. 13/793,390 dated Jan. 11, 2018 (11 pages).
"Final Office Action," for U.S. Appl. No. 13/793,390 dated Sep. 7, 2017 (9 pages).
"Final Office Action," for U.S. Appl. No. 14/280,170 dated Nov. 1, 2017 (50 pages).
"Final Office Action," for U.S. Appl. No. 14/609,270 dated Dec. 8, 2015 (27 pages).
"Final Office Action," for U.S. Appl. No. 15/357,496 dated Sep. 20, 2017 (8 pages).
"Final Office Action," for U.S. Appl. No. 15/385,112 dated Aug. 24, 2017 (13 pages).
"Final Rejection," from CN Application No. 201080018767.7, dated Jan. 6, 2014 (10 pages).
Finkel, Toren "Relief with Rapamycin: mTOR Inhibition Protects Against Radiation-Induced Mucositis," Cell Stem Cell, vol. 11:3, Sep. 7, 2012 (pp. 1-4).
"First Office Action," for Chinese Application No. 201080018767.7 dated Jun. 8, 2013 (9 pages).
"First Office Action," for Chinese Patent Application No. 2012800328049, dated Mar. 2, 2015 (12 pages) including English translation.
"First Office Action," for Chinese Patent Application No. 201510411761.0 dated Jun. 30, 2017 (13 pages) with English translation.

"Fourth Office Action," for Chinese Patent Application No. 2012800328049, dated May 3, 2017 (8 pages) with English translation.
Ghonaim, Hassan M. et al., "N1,N12-Diacyl Spermines: SAR Studies on Non-viral Lipopolyamine Vectors for Plasmid DNA and siRNA Formulation," Pharmaceutical Research, vol. 27, No. 1, Jan. 2010 (p. 17-29) Oct. 30, 2009.
"International Preliminary Report on Patentability," for PCT Application No. PCT/US2016/015644 dated Aug. 10, 2017 (12 pages).
"International Preliminary Report on Patentability," for PCT/US2012/038158, dated Nov. 28, 2013 (8 pages).
"International Preliminary Report on Patentability," for PCT/US2013/068539, dated May 14, 2015 (9 pages).
"International Preliminary Report on Patentability," for PCT/US2014/038435 dated Nov. 26, 2015 (10 pages).
"International Search Report & Written Opinion," for PCT/US2016/015644 dated Jul. 11, 2016 (17 pages).
"International Search Report and Written Opinion," for PCT Application No. PCT/US2017/066573 dated Apr. 3, 2018 (10 pages).
"International Search Report and Written Opinion," for PCT/US2010/032741 dated Dec. 13, 2010 (11 pages). Dec. 13, 2010, 11 pages.
"International Search Report and Written Opinion," for PCT/US2012/038158, dated Sep. 27, 2012 (13 pages).
"International Search Report and Written Opinion," for PCT/US2013/068539, dated Jan. 22, 2014 (12 pages).
"International Search Report and Written Opinion," for PCT/US2014/038435, dated Aug. 25, 2014 (13 pages).
"Invitation to Pay Additional Fees and Partial Search Report," for PCT Application No. PCT/US2016/015644, dated May 3, 2016 (8 pages).
"Invitation to Respond to Written Opinion," for SG Patent Application No. 201107896-1, dated Jun. 12, 2012 (6 pages).
Liu, Rong "Water-Insoluble Drug Formulation," CRC Press, 2nd Ed., 2008 (pp. 1-3).
Love, Kevin T. et al., "Lipid-Like Materials for Low-Dose In Vivo Gene Silencing," PNAS Feb. 2010, 107 (5) 1864-1869, www.pnas.org/cgi/doi/10.1073/pnas.0910603106 (6 pages).
Mugabe, Clement et al., "Paclitaxel Incorporated in Hydrophobically Derivated Hyperbranched Polyglycerols for Intravesical Bladder Cancer Therapy," BJU International, 2008, vol. 103, p. 978-986.
"Non-Final Office Action," for Japanese Patent Application No. 2012-508637, dated Mar. 18, 2014 (4 pages) with English translation.
"Non-Final Office Action," for Mexican Patent Application No. MX/a/2011/011389, dated Aug. 18, 2015 (1 page).
"Non-Final Office Action," for Mexican Patent Application No. MX/a/2011/011389, dated Feb. 22, 2016 (1 page).
"Non-Final Office Action," for U.S. Appl. No. 14/280,170 dated Apr. 6, 2017 (54 pages).
"Non-Final Office Action," for U.S. Appl. No. 14/609,270 dated Apr. 10, 2017 (24 pages.).
"Non-Final Office Action," for U.S. Appl. No. 14/609,270 dated Aug. 3, 2016 (14 pages).
"Non-Final Office Action," for U.S. Appl. No. 15/357,496 dated Mar. 9, 2017 (8 pages).
"Non-Final Office Action," for U.S. Appl. No. 15/385,112 dated Jan. 11, 2018 (11 pages).
"Non-Final Office Action," for U.S. Appl. No. 15/385,112, dated Feb. 24, 2017 (14 pages).
"Non-Final Office Action," for U.S. Appl. No. 15/850,010 dated Jan. 24, 2018 (7 pages).
"Notice of Allowance," for U.S. Appl. No. 13/469,844 dated Mar. 24, 2017 (10 pages).
"Notice of Allowance," for U.S. Appl. No. 14/609,270 dated Sep. 7, 2017 (21 pages).
"Notice of Allowance," for U.S. Appl. No. 15/357,496 dated Feb. 7, 2018 (36 pages).
"Notification for Patent Reexamination," for Chinese Patent Application No. 201080018767.7, dated Sep. 25, 2014 (12 pages) with English translation.
"Office Action," for Canadian Patent Application No. 2,760,187 dated Jan. 12, 2017 (3 pages).

(56) References Cited

OTHER PUBLICATIONS

"Office Action," for Canadian Patent Application No. 2,760,187 dated Mar. 24, 2016 (4 pages).
"Office Action," for Canadian Patent Application No. 2,836,266 dated Apr. 11, 2018 (3 pages).
"Office Action," for Japanese Patent Application No. 2014511494 dated Feb. 5, 2016 (13 pages) with English Translation.
"Office Action," for Japanese Patent Application No. 2014511494 dated Nov. 25, 2016 (6 pages) with English Translation.
"Office Action," for Japanese Patent Application No. 2015-540868 dated Aug. 31, 2017 (10 pages) with English translation.
"Office Action," for Japanese Patent Application No. 2015-540868 dated May 21, 2018 (6 pages) with English translation.
"Office Action," for Japanese Patent Application No. 2016-514136 dated Apr. 10, 2018 (7 pages) with English translation.
"PCT Notification Concerning Transmittal of International Preliminary Report on Patentability," from International Application No. PCT/US10/032741, corresponding to U.S. Appl. No. 61/173,462, dated Nov. 10, 2011, pp. 1-8, 8.
"Response to Communication Pursuant to Article 94(3) EPC," for European Application No. 10716714.0 filed with EPO Aug. 11, 2015 (51 pages).
"Response to Communication Pursuant to Article 94(3) EPC," for European Application No. 10716714.0 filed with EPO Jun. 10, 2013 (9 pages).
"Response to Communication Pursuant to Article 94(3) EPC," for European Patent Application No. 12723063.9 filed with the EPO Nov. 16, 2017 (9 pages).
"Response to Communication Pursuant to Article 94(3) EPC," for European Patent Application No. 13792207.6, filed with the EPO Mar. 29, 2018 (25 pages).
"Response to Communication Pursuant to Article 94(3) EPC," for European Patent Application No. 14730381.2, filed with the European Patent Office Dec. 21, 2017 (68 pages).
"Response to Communication Pursuant to Rule 161 and 162 EPC," for European Patent Application 12723063.9, dated Jan. 21, 2014 and filed with the EPO Jul. 18, 2014 (4 pages).
"Response to Communication Pursuant to Rules 161(1) and 162 EPC," for European Patent No. 16703247.3 filed with the EPO on Mar. 22, 2018.
"Response to Final Office Action," for U.S. Appl. No. 13/793,390, dated Sep. 7, 2017 and filed Dec. 7, 2017 (20 pages).
"Response to Final Office Action," for U.S. Appl. No. 15/385,112, dated Aug. 24, 2017 and filed Nov. 22, 2017 (13 pages).
"Response to Final Office Action," for U.S. Appl. No. 13/469,844, dated Feb. 24, 2015 and filed Jul. 24, 2015 (7 pages).
"Response to Final Office Action," for U.S. Appl. No. 13/793,390, dated Jan. 11, 2018 and filed Jun. 11, 2018 (17 pages).
"Response to Final Office Action," for U.S. Appl. No. 14/280,170, dated Nov. 1, 2017 and filed Feb. 1, 2018 (26 pages).
"Response to Final Office Action," for U.S. Appl. No. 14/609,270, dated Dec. 8, 2015 and filed Apr. 1, 2016 (12 pages).
"Response to Final Office Action," for U.S. Appl. No. 15/357,496, dated Sep. 20, 2017 and filed Dec. 20, 2017 (6 pages).
"Response to Final Office Action," for U.S. Appl. No. 13/793,390, mailed Dec. 19, 2016 and filed May 19, 2017 (20 pages).
"Response to Non-Final Office Action," for U.S. Appl. No. 14/280,170, dated Apr. 6, 2017 and filed Jul. 21, 2017 (16 pages).
"Response to Non-Final Office Action," for U.S. Appl. No. 14/609,270, dated Apr. 10, 2017 and filed Jul. 21, 2017 (15 pages).
"Response to Non-Final Office Action," for U.S. Appl. No. 14/609,270, dated Aug. 3, 2016 and filed Dec. 15, 2016 (12 pages).
"Response to Non-Final Office Action," for U.S. Appl. No. 15/357,496, dated Mar. 9, 2017 and filed Jun. 9, 2017 (9 pages).
"Response to Non-Final Office Action," for U.S. Appl. No. 15/385,112, filed Apr. 20, 2018 (15 pages) for Non-Final Office Action dated Jan. 11, 2018.
"Response to Non-Final Office Action," for U.S. Appl. No. 15/385,112, dated Feb. 24, 2017 and filed May 19, 2017 (10 Pages).
"Response to Non-Final Office Action," for U.S. Appl. No. 15/850,010, dated Jan. 24, 2018 and filed Jun. 11, 2018 (8 pages).
"Response to Office Action," for Canadian Patent Application No. 2,760,187 filed with CIPO Feb. 15, 2017 (5 pages).
"Response to Office Action," for Canadian Patent Application No. 2,760,187 filed with CIPO Sep. 22, 2016 (22 pages).
Salamone, Joseph "Hydrophic Polymers (for Friction Reduction)," Polymeric Materials Encyclopedia, vol. 12 (1996) p. 3107.
Scheller, Bruno et al., "Paclitaxel Balloon Coating, a Novel Method for Prevention and Therapy of Restenosis," Circulation, Journal of the American Heart Association; 2004 (110);810-814. Online version of article: http://circ.ahajournals.org/cgi/content/full/11/7/810, downloaded Jan. 12, 2011 2004, 6 pages.
"Second Office Action," for China Patent Application No. 2012800328049, dated Jan. 26, 2016 (9 pages), with translation.
"Second Office Action," for Chinese Patent Application No. 201510411761.0 dated Dec. 22, 2017 (11 pages) with English translation.
"Third Office Action," for Chinese Patent Application No. 2012800328049, dated Aug. 11, 2016 (12 pages) with English translation.
"Decision of Rejection," for Chinese Patent Application No. 201510411761.0 dated Nov. 30, 2018 (19 pages) with English Translation.
"Non-Final Office Action," for U.S. Appl. No. 15/840,540 dated Oct. 17, 2018 (38 pages).
"Notice of Allowance," for U.S. Appl. No. 13/793,390 dated Oct. 31, 2018 (10 pages).
"Office Action," for Canadian Patent Application No. 2,836,266 dated Nov. 30, 2018 (4 pages).
"Product Data Sheet," for PEBAX MV 1074 SA 01 MED from Arkema (2013, pp. 1-2) 2 pages.
"Response to Communication Pursuant to Article 94(3) EPC," for European Patent Application No. 16703247.3 filed Dec. 20, 2018 (7 pages).
"Response to Non-Final Office Action," for U.S. Appl. No. 14/280,170, filed Dec. 10, 2018 (18 pages).
"Response to Non-Final Office Action," for U.S. Appl. No. 15/840,540, filed Dec. 20, 2018 (9 pages).
"Communication Pursuant to Article 94(3) EPC," for European Patent Application No. 16703247.3 dated Sep. 4, 2018 (5 pages).
"Final Office Action," for U.S. Appl. No. 15/850,010 dated Oct. 2, 2018 (35 pages).
"First Examination Report," for Indian Patent Application No. 3723/KOLNP/2013 dated Sep. 28, 2018 (5 pages).
"Non Final Office Action," for U.S. Appl. No. 14/280,170 dated Oct. 5, 2018 (36 pages).
"Non-Final Office Action," for U.S. Appl. No. 13/793,390 dated Jul. 13, 2018 (48 pages).
"Non-Final Office Action," for U.S. Appl. No. 15/385,112 dated Aug. 13, 2018 (8 pages).
"Notice of Allowance," for U.S. Appl. No. 15/385,112 dated Oct. 5, 2018 (10 pages).
"Office Action," for Mexican Patent Application No. MX/a/2015/015589 dated Sep. 9, 2018 (1 page), translation only.
"Response to Non-Final Rejected," dated Aug. 13, 2018, for U.S. Appl. No. 15/385,112, filed Sep. 12, 2018, 5 pages.
"Response to Non-Final Rejection," dated Jul. 13, 2018, for U.S. Appl. No. 13/793,390, filed Sep. 12, 2018, 6 pages.
"Response to Office Action," for Canadian Patent Application No. 2,836,266 filed with CIPO Sep. 20, 2018 (28 pages).
"Third Office Action," for Chinese Patent Application No. 201510411761.0 dated Jul. 25, 2018 (14 pages) with English translation.
"First Office Action," for Russian Patent Application No. 2017129933 dated Jun. 27, 2019 (10 pages) with English Translation.
"International Preliminary Report on Patentability," for PCT Application No. PCT/US2017/066573 dated Jul. 4, 2019 (7 pages).
"Non-Final Office Action," for U.S. Appl. No. 15/840,540 dated Aug. 20, 2019 (20 pages).
"Notice of Allowance," for U.S. Appl. No. 15/850,010 dated Oct. 23, 2019 (14 pages).

(56) References Cited

OTHER PUBLICATIONS

"Office Action Response," for Israeli Patent Application No. 242545 filed Sep. 28, 2019 (133 pages) English Translation.

"Office Action," for Canadian Patent Application No. 2,890,205 dated Sep. 18, 2019 (5 pages).

"Preliminary Office Action," for Brazilian Patent Application No. 1120170136420 dated Oct. 15, 2019 (7 pages) with English Translation.

"Response to communication Pursuant to Article 94(3) EPC," for European Patent Application No. 12723063.9 filed Jul. 2, 2019 (56 pages).

"Response to Communication Pursuant to Article 94(3) EPC," for European Patent Application No. 16703247.3 filed Aug. 30, 2019 (10 pages).

"Response to Final Rejection," dated Apr. 5, 2019 for U.S. Appl. No. 14/280,170, filed Aug. 2, 2019, 12 pages.

"Response to Non-Final Rejection," dated Feb. 26, 2019 for U.S. Appl. No. 15/850,010, filed Jun. 26, 2019, 6 pages.

Chen, Xia-Chao et al., "Humidity-Triggered Self-Healing of Microporous Polyelectrolyte Multilayer Coatings for Hydrophobic Drug Delivery," Advanced Functional Materials, vol. 25, No. 48, Dec. 1, 2015 pp. 7470-7477 (8 pages).

"Communication Pursuant to Article 94(3) EPC," for European Patent Application No. 16703247.3 dated Feb. 12, 2020 (7 pages).

"Final Office Action," for U.S. Appl. No. 15/840,540 dated Dec. 11, 2019 (22 pages).

"First Examination Report," for Indian Patent Application No. 201747029823 dated Nov. 25, 2019 (6 pages).

"First Office Action," for Chinese Patent Application No. 2016800187265 dated Nov. 5, 2019 (9 pages) with English Translation.

"Non-Final Office Action," for U.S. Appl. No. 14/280,170 dated Apr. 15, 2020 (32 pages).

"Non-Final Office Action," for U.S. Appl. No. 15/840,540 dated Mar. 30, 2020 (22 pages).

"Office Action," for Canadian Patent Application No. 2,836,266 dated Oct. 23, 2019 (3 pages).

"Office Action," for Israeli Patent Application No. 242545 dated Feb. 6, 2020 (7 pages) with English Translation.

"Office Action," for Japanese Patent Application No. 2017-540169 dated Nov. 21, 2019 (12 pages) with English Translation.

"Office Action," for Russian Patent Application No. 2017129933 dated Mar. 2, 2020 (9 pages) with English Translation.

"Office Action," for Russian Patent Application No. 2017129933 dated Oct. 21, 2019 (9 pages) with English Translation.

"Response to Communication Pursuant to Rules 161(1) and 162 EPC," for European Patent Application No. 17835893.3 filed Jan. 21, 2020 (7 pages).

"Response to Final Office Action," for U.S. Appl. No. 15/840,540, filed Mar. 5, 2020 (13 pages).

"Response to Non-Final Office Action," for U.S. Appl. No. 15/840,540, filed Nov. 20, 2019 (13 pages).

"Response to Office Action," for Canadian Patent Application No. 2,836,266 filed Apr. 15, 2020 (18 pages).

"Response to Office Action," for Canadian Patent Application No. 2,890,205 filed Mar. 18, 2020 (28 pages).

"Written Submissions in Respect of Hearing on Nov. 14, 2019," for Indian Patent Application No. 3723/KOLNP/2013 filed Nov. 23, 2019 (19 pages).

"Communication Pursuant to Article 94(3) EPC," for European Patent Application No. 17835893.3 dated Jun. 29, 2020 (5 pages).

"Notice of Allowance," for U.S. Appl. No. 15/840,540 dated Sep. 16, 2020 (18 pages).

"Office Action," for Canadian Patent Application No. 2,836,266 dated Jul. 23, 2020 (3 pages).

"Office Action," for Canadian Patent Application No. 2,912,690 dated Apr. 29, 2020 (5 pages).

"Office Action," for Israeli Patent Application No. 253612 dated Jul. 31, 2020 (8 pages) with English Translation.

"Office Action," for Japanese Patent Application No. 2017-540169 dated Jul. 30, 2020 (9 pages) with English Translation.

"Office Action," for Mexican Patent Application No. MX/a/2017/009688 dated Jul. 14, 2020 (5 pages) with English Translation.

"Reexamination Notification," for Chinese Patent Application No. 201510411761.0 dated Jun. 3, 2020 (13 pages) with English Translation.

"Response to Communication Pursuant to Article 94(3) EPC," for European Patent Application No. 16703247.3 filed Aug. 11, 2020 (10 pages).

"Response to First Examination Report," for Indian Patent Application No. 201747029823 filed May 22, 2020 (13 pages).

"Response to Non-Final Office Action," for U.S. Appl. No. 14/280,170, filed Jul. 14, 2020 (11 pages).

"Response to Non-Final Office Action," for U.S. Appl. No. 15/840,540, filed Jul. 23, 2020 (15 pages).

"Response to Office Action," for Canadian Patent Application No. 2,912,690 filed Aug. 13, 2020 (39 pages).

"Response to Office Action," for Israeli Patent Application No. 242545 filed Jun. 7, 2020 (15 pages).

"Second Office Action," for Chinese Patent Application No. 2016800187265 dated Jun. 10, 2020 (10 pages) with English Translation.

* cited by examiner under 2014 # DEVICES AND METHODS FOR DELIVERY OF BIOACTIVE AGENTS This application is a continuation application of U.S. application Ser. No. 12/769,127, filed Apr. 28, 2010, which claims the benefit of U.S. Provisional Application No. 61/173,462, filed Apr. 28, 2009, the contents of which are herein incorporated by reference.

FIELD OF THE INVENTION

The present invention relates to devices and methods for the delivery of bioactive agents. More specifically, the present invention relates to devices and methods for the delivery of bioactive agents from the surface of a hydrophilic polymer.

BACKGROUND OF THE INVENTION

The release of bioactive agents from an implanted medical device has been shown to be beneficial for the function of devices and the treatment of various medical conditions. For example, delivery of a bioactive agent from a device can prevent cellular responses initiated by the presence of the implantable device. Bioactive agents released from the device can also prevent conditions that would otherwise shorten the functional life of the device following implantation. A bioactive agent released from the device may also be directed at treating a diseased area of the body.

SUMMARY OF THE INVENTION

Embodiments of the invention include bioactive agent eluting devices. In an embodiment the invention includes a bioactive agent delivery device including a substrate, a hydrophilic polymer disposed on the substrate, and a substantially amorphous bioactive agent disposed on the surface of the hydrophilic polymer.

In an embodiment, the invention includes a method of making a bioactive agent delivery device including depositing a hydrophilic polymer on a substrate forming a hydrophilic surface and depositing a substantially amorphous bioactive agent on the hydrophilic surface.

In an embodiment, the invention includes a bioactive agent-eluting catheter including a catheter shaft and an expandable balloon disposed on the catheter shaft. A hydrophilic polymer can be disposed on the outside surface of the balloon and a substantially amorphous bioactive agent can be disposed on the surface of the hydrophilic polymer.

The above summary of the present invention is not intended to describe each discussed embodiment of the present invention. This is the purpose of the figures and the detailed description that follows.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

In an embodiment the invention includes a method of making a bioactive agent delivery device. The method can include depositing a hydrophilic polymer on a substrate forming a hydrophilic surface; and depositing a substantially amorphous bioactive agent on the hydrophilic surface. In some embodiments, depositing the hydrophilic polymer on the substrate can include depositing a photo-polymer on the substrate, the photo-polymer comprising latent photoreactive groups and a hydrophilic backbone; and applying actinic radiation to the photo-polymer. The use of a photo-polymer can result in formation of covalent bonds between the hydrophilic polymer and substrate leading to a structurally secure coating.

While not intending to be bound by theory, it is believed that release of the bioactive agent can be enhanced by preventing the formation of an interpenetrating network between the hydrophilic polymer and the bioactive agent composition. As described herein, the use of a solvent when depositing the bioactive agent that does not solvate the hydrophilic polymer can prevent the formation of an interpenetrating network between the hydrophilic polymer and the bioactive agent. By way of example, if the hydrophilic polymer is strongly water soluble then a solvent (such as a non-polar solvent, depending on the particular hydrophilic polymer) can be used when depositing the bioactive agent without formation of an interpenetrating network. In an embodiment, a method includes the operation of selecting a solvent that does not solvate the hydrophilic polymer.

Embodiments herein can also include devices, such as devices with an expandable balloon that can deliver a bioactive agent. In particular, embodiments herein can include expandable balloons including a base layer of a hydrophilic polymer and top layer of a substantially amorphous bioactive agent disposed on the hydrophilic polymer. In some embodiments, the amorphous bioactive agent can be hydrophobic.

Figure 1:
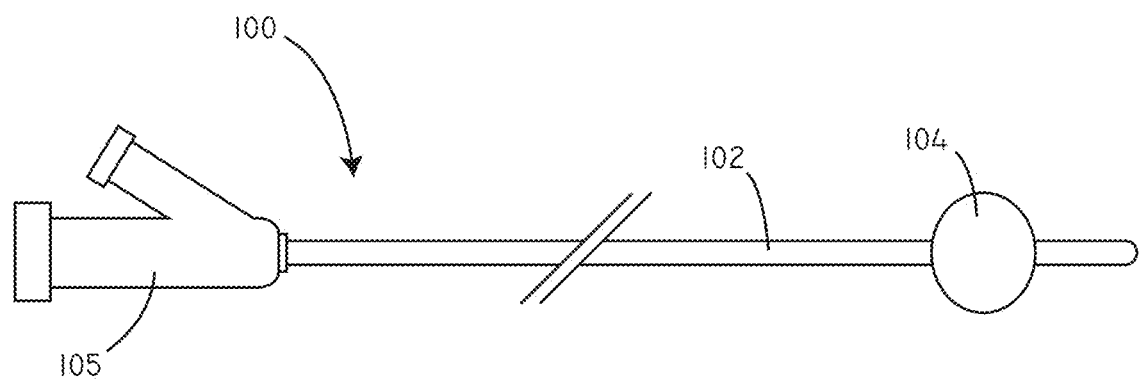
FIG. 1 is a schematic view of a device in accordance with an embodiment herein.

Referring now to FIG. 1, a schematic view of an exemplary device is shown in accordance with an embodiment. The device 100 can be, for example, an angioplasty balloon catheter. However, further examples of exemplary devices are described in greater detail below. The device 100 includes a catheter shaft 102 and a manifold end 105. The device 100 also includes an inflatable balloon 104 disposed around the catheter shaft 102. In FIG. 1, the balloon 104 is shown in an inflated configuration. The catheter shaft 102 can include a channel to convey air through the catheter shaft 102 and to or from the balloon 104, so that the balloon 104 can selectively go from a deflated configuration to the inflated configuration and back again.

Figure 2:
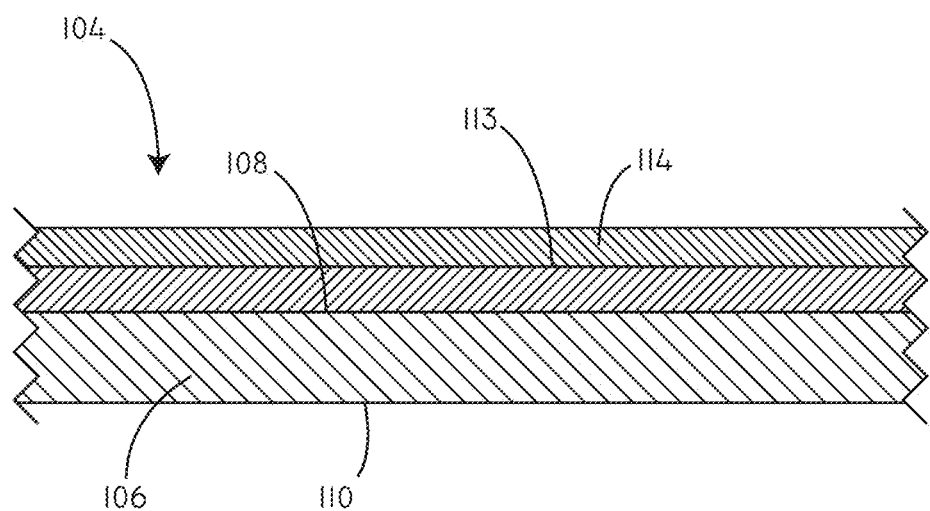
FIG. 2 is a schematic cross-sectional view of a portion of a device in accordance with an embodiment herein.

FIG. 2 shows a schematic cross-sectional view of a portion of the device in accordance with an embodiment herein. Specifically, FIG. 2 shows a cross-sectional view of the expandable balloon 104. The expandable balloon 104 can include a substrate 106 having an inner surface 110 and an outer surface 108. A hydrophilic polymer layer 112 (base layer or base coat) can be disposed on the outer surface 108 of the substrate 106. The hydrophilic polymer layer 112 can include a hydrophilic surface 113. A substantially amorphous bioactive agent layer (top layer or top coat) can be disposed on the hydrophilic surface 113 of the hydrophilic polymer layer 112.

The substrate 106 can be formed from any material, or combination of materials, capable of expanding, and suitable for use within the body. The one or more material(s) can be based on use of the device. In many embodiments the expandable materials are compliant and flexible materials, such as elastomers (polymers with elastic properties). Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, polyether-polyamide copolymers, and the like. The substrate 106 can be made of a single elastomeric material, or a combination of materials.

The substrate 106 can have a thickness suitable for the desired application and device. For example, the thickness of the substrate 106 can be in the range of about 5 μm to about 100 μm. Exemplary thicknesses for the walls of catheter balloons are in the range of about 5 μm to about 20 μm. The actual thickness of the balloon wall may depend on one or more factors, such as the desired pliability of the balloon, the overall profile of the balloon on the catheter (low profile devices may use thin walled balloons), the pressure rating for the balloon wall, or the expansion properties of the balloon.

The manufacture of expandable substrates is well known in the art, and any suitable process can be carried out to provide the expandable substrate portion of the insertable medical device as described herein. Catheter balloon construction is described in various references, for example, U.S. Pat. Nos. 4,490,421, 5,556,383, 6,210,364, 6,168,748, 6,328,710, and 6,482,348. Molding processes are typically performed for balloon construction. In an exemplary molding process, an extruded polymeric tube is radially and axially expanded at elevated temperatures within a mold having the desired shape of the balloon. The balloon can be subjected to additional treatments following the molding process. For example, the formed balloon can be subjected to additional heating steps to reduce shrinkage of the balloon.

Referring back to FIG. 1, the insertable medical device 100 can also have one or more non-expandable (or inelastic) portions. For example, in a balloon catheter, the catheter shaft 102 portion can be the non-expandable portion. The non-expandable portion can be partially or entirely fabricated from a polymer. Polymers include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

The non-expandable portion can also be partially or entirely fabricated from a metal. Metals that can be used in medical articles include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

Methods of Forming the Hydrophilic Polymer Layer

In some embodiments, a hydrophilic polymer solution is formed by combining a hydrophilic polymer with a solvent. Exemplary hydrophilic polymers are described in greater detail below. The hydrophilic polymer solution can then be applied to a suitable substrate, such as an expandable balloon disposed on a catheter shaft. Many different techniques can be used to apply the hydrophilic polymer solution to the substrate. By way of example, exemplary techniques can include drop coating, blade coating, dip coating, spray coating, and the like. Aspects and details of a balloon coating apparatus and method can be found in commonly owned provisional Application having Ser. No. 61/188,929, filed on Aug. 14, 2008, and entitled METHOD AND APPARATUS FOR COATING BALLOON CATHETERS (Chappa et al.).

In some embodiments, such as where a photo-polymer is used to form the hydrophilic layer, an actinic radiation application step can be performed in order to activate latent photoreactive groups on the hydrophilic polymer or on a cross-linker in order to covalently bond the hydrophilic polymer the substrate surface. By way of example, after applying the hydrophilic polymer solution to the substrate, the device can be subjected to UV exposure at a desirable wavelength for a period of time.

Hydrophilic Biocompatible Polymers

One class of hydrophilic polymers useful as polymeric materials for matrix formation is synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these.

Examples of polymers that can be formed from these monomers include poly(acrylamide), poly(methacrylamide), poly(vinylpyrrolidone), poly(acrylic acid), poly(ethylene glycol), poly(vinyl alcohol), and poly(HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,N-dimethylacrylamide-co-aminopropylmethacrylamide) and poly(acrylamide-co-N,N-dimethylaminopropylmethacrylamide) are described in example 2 of Applicants' co-pending U.S. Patent Pub. No. 2006/0030669 filed Sep. 17, 2004 (Taton et al.). In some embodiments, the hydrophilic polymer is a vinyl pyrrolidone polymer, or a vinyl pyrrolidone/(meth)acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth)acrylamide derivatives, such as alkyl(meth)acrylamide, as exemplified by dimethylacrylamide, and aminoalkyl(meth)acrylamide, as exemplified by aminopropylmethacrylamide and dimethylaminopropylmethacrylamide. For example, poly(vinylpyrrolidone-co-N,N-dimethylaminopropylmethacrylamide) is described in example 2 of U.S. Patent Pub. No. 2006/0030669 (Taton et al.).

Photo-Polymers and Cross-Linkers of the Hydrophilic Layer

Embodiments herein can include the use of photo-polymers to form a hydrophilic polymer layer covalently bonded to a desired substrate. Photo-polymers as used herein can include one or more photoreactive groups covalently bonded to a polymeric backbone. Embodiments herein can also include the of a photo-reactive cross-linking reagent in order to covalently bond a hydrophilic polymer layer to a desired substrate.

As such, embodiments herein can include the use of compounds with photoreactive groups. As used herein, the phrases "latent photoreactive group" and "photoreactive group" are used interchangeably and refer to a chemical moiety that is sufficiently stable to remain in an inactive state (i.e., ground state) under normal storage conditions but that can undergo a transformation from the inactive state to an activated state when subjected to an appropriate energy source. Photoreactive groups respond to specific applied external stimuli to undergo active specie generation with resultant covalent bonding to an adjacent chemical structure. For example, in an embodiment, a photoreactive group can be activated and can abstract a hydrogen atom from an alkyl group. A covalent bond can then form between the compound with the photoreactive group and the compound with the C—H bond. Suitable photoreactive groups are described in U.S. Pat. No. 5,002,582, the disclosure of which is incorporated herein by reference.

Photoreactive groups can be chosen to be responsive to various portions of actinic radiation. Typically, groups are chosen that can be photoactivated using either ultraviolet or visible radiation. Suitable photoreactive groups include, for example, azides, diazos, diazirines, ketones, and quinones. The photoreactive groups generate active species such as free radicals including, for example, nitrenes, carbenes, and excited states of ketones upon absorption of electromagnetic energy.

In some embodiments, the photoreactive group is an aryl ketone, such as acetophenone, benzophenone, anthrone, and anthrone-like heterocycles (i. e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photoreactive groups include quinone such as, for example anthraquinone.

The functional groups of such aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (from a polymeric coating layer, for example), thus creating a radical pair. Subsequent collapse of the radical pair leads to formation of a new carbon-carbon bond. If a reactive bond (e.g., carbon/hydrogen) is not available for bonding, the ultraviolet light-induced excitation of the benzophenone group is reversible and the molecule returns to ground state energy level upon removal of the energy source. Photoreactive aryl ketones such as benzophenone and acetophenone can undergo multiple reactivations in water and hence can provide increased coating efficiency.

The azides constitute another class of photoreactive groups and include arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$—CO—O—) such as t-butyl alpha diazoacetoacetate.

Other photoreactive groups include the diazirines (—$CHN_2$) such as 3-trifluoromethyl-3-phenyldiazirine; and ketenes (—CH=C=O) such as ketene and diphenylketene.

The polymeric backbone of the photo-polymer can provide desirable physical properties to the substrate to which it is bonded. In various embodiments herein, the polymeric backbone is selected so as to provide a hydrophilic surface on the substrate. It will be appreciated that many different types of polymeric backbones may provide a hydrophilic surface. Exemplary polymers can include, but are not limited to, hyaluronic acid, polyvinyl alcohol, polyvinylpyrrolidone, polyethylene glycol, collagen, chitosan, and the like.

By way of example, methods for the preparation of photo-PVP are described in U.S. Pat. No. 5,414,075. Methods for the preparation of photo-polyacrylamide are described in U.S. Pat. No. 6,007,833.

Methods of Depositing the Bioactive Agent

In many embodiments, the bioactive agent is applied from a solution or mixture. The solution or mixture can be formed by combining the bioactive agent and a solvent. Optionally, one or more additives can also be added to form the bioactive agent solution or mixture. In some embodiments, the bioactive agent solution or mixture can include more than one bioactive agent. In some embodiments, the bioactive agent solution or mixture can include more than one solvent.

The solvent can be selected based on the particular hydrophilic polymer used as the base layer or base coat. In some embodiments, the solvent selected is one that does not solvate the particular hydrophilic polymer used as the base layer or base coat (e.g., the solvent of the bioactive agent solution or mixture is not effective as a solvent for the hydrophilic polymer) at temperature and pressure conditions such as standard room temperature and pressure (e.g., approximately 72 degrees Fahrenheit or 22 degrees Celsius and 760 mmHg). Stated alternately, in some embodiments the hydrophilic polymer is not soluble in the solvent of the bioactive agent composition. By using a solvent for the bioactive agent composition that does not solvate the hydrophilic polymer, formation of an interpenetrating network between the hydrophilic polymer and the bioactive agent can be prevented. As such, the bioactive agent composition can be disposed on the surface of the hydrophilic polymer without penetrating into the hydrophilic polymer in any substantial way.

As an example, if poly(vinylpyrrolidone) is used as the hydrophilic polymer of the base layer, then a solvent such as ethyl acetate can be used as the solvent for the bioactive agent solution or mixture, because it does not serve as a solvent to poly(vinylpyrrolidone). For certain hydrophilic polymers, possible solvents can include, but are not limited to, nonpolar solvents. It will be appreciated, though, that some hydrophilic polymers may have solubility in some nonpolar solvents.

After the bioactive agent solution or mixture is formed, it can be applied to the surface of the hydrophilic polymer layer. Many different techniques can be used to apply the bioactive agent solution. By way of example, exemplary techniques can include drop coating, blade coating, dip coating, spray coating, and the like. After application, the residual solvent form the bioactive agent solution or mixture can be evaporated off.

Bioactive Agents

The term "bioactive agent," refers to an inorganic or organic molecule, which can be synthetic or natural, that causes a biological effect when administered in vivo to an animal, including but not limited to birds and mammals, including humans. A partial list of bioactive agents is provided below. In some embodiments these bioactive agents may be used alone, in other embodiments these bioactive agents may be used in combination with one another. A comprehensive listing of bioactive agents, in addition to information of the water solubility of the bioactive agents, can be found in *The Merck Index*, Thirteenth Edition, Merck & Co. (2001).

It will be appreciated that many of the exemplary bioactive agents listed below can be formulated in different ways. For example, many (but not all) of the bioactive agents listed below can exist in both crystalline and amorphous forms. In various embodiments herein, the bioactive agents are used in a substantially amorphous form. As used herein, substantially amorphous shall refer to active agents that are at least 60% in amorphous form by weight. In some embodiments, amorphous bioactive agents herein can be at least 80% in amorphous form by weight. In some embodiments, amorphous bioactive agents herein can be at least 95% in amorphous form by weight. While not intending to be bound by theory, it believed that delivery in amorphous form can be advantageous in terms of both release kinetics as well as uptake by the tissue at the delivery site. In various embodiments, the bioactive agent is a relatively hydrophobic active agent. Hydrophobicity of a bioactive agent can be assessed base on its solubility in water. As used herein, hydrophobic bioactive agents have a water solubility of less than about 0.001 mg/ml.

Exemplary bioactive agents can include those falling within one or more of the following classes, which include, but are not limited to, ACE inhibitors, actin inhibitors, analgesics, anesthetics, anti-hypertensives, anti polymerases, antisecretory agents, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, prostaglandins, remodeling inhibitors, statins, steroids, thrombolytic agents, tranquilizers, vasodilators, and vasospasm inhibitors.

In some aspects the bioactive agent includes an antiproliferative agent. The antiproliferative agent can be an antiangiogenesis agent. In some aspects the bioactive agent includes an anti-inflammatory agent. In some aspects the bioactive agent includes a cell response modifier. In some aspects the bioactive agent includes an anti-thrombotic agent. In some aspects the bioactive agent includes an immunosuppressive agent.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins.

Examples of statins include lovastatin, pravastatin, simvastatin, fluvastatin, atorvastatin, cerivastatin, rosuvastatin, and superstatin.

Examples of steroids include glucocorticoids such as cortisone, hydrocortisone, dexamethasone, betamethasone, prednisone, prednisolone, methylprednisolone, triamcinolone, beclomethasone, fludrocortisone, and aldosterone; sex steroids such as testosterone, dihydrotestosterone, estradiol, diethylstilbestrol, progesterone, and progestins.

The bioactive agent can provide antirestenotic effects, such as antiproliferative, anti-platelet, and/or antithrombotic effects. In some embodiments, the bioactive agent can be selected from anti-inflammatory agents, immunosuppressive agents, cell attachment factors, receptors, ligands, growth factors, antibiotics, enzymes, nucleic acids, and the like. Compounds having antiproliferative effects include, for example, actinomycin D, angiopeptin, c-myc antisense, paclitaxel, taxane, and the like.

Representative examples of bioactive agents having antithrombotic effects include heparin, heparin derivatives, sodium heparin, low molecular weight heparin, hirudin, lysine, prostaglandins, argatroban, forskolin, vapiprost, prostacyclin and prostacyclin analogs, D-phe-pro-arg-chloromethylketone (synthetic antithrombin), dipyridamole, glycoprotein IIb/IIIa platelet membrane receptor antibody, coprotein IIb/IIIa platelet membrane receptor antibody, recombinant hirudin, thrombin inhibitor (such as commercially available from Biogen), chondroitin sulfate, modified dextran, albumin, streptokinase, tissue plasminogen activator (TPA), urokinase, nitric oxide inhibitors, and the like.

The bioactive agent can also be an inhibitor of the GPIIb-IIIa platelet receptor complex, which mediates platelet aggregation. GPIIb/IIIa inhibitors can include monoclonal antibody Fab fragment c7E3, also know as abciximab (ReoPro™), and synthetic peptides or peptidomimetics such as eptifibatide (Integrilin™) or tirofiban (Agrastat™).

The bioactive agent can be an immunosuppressive agent, for example, cyclosporine, CD-34 antibody, everolimus, mycophenolic acid, sirolimus (rapamycin), rapalogs (analogues of rapamycin), tacrolimus, and the like.

Additionally, the bioactive agent can be a surface adhesion molecule or cell-cell adhesion molecule. Exemplary cell adhesion molecules or attachment proteins, such as extracellular matrix proteins, include fibronectin, laminin, collagen, elastin, vitronectin, tenascin, fibrinogen, thrombospondin, osteopontin, von Willibrand Factor, bone sialoprotein (and active domains thereof), and hydrophilic polymers such as hyaluronic acid, chitosan and methyl cellulose, and other proteins, carbohydrates, and fatty acids. Other cell-cell adhesion molecules include N-cadherin and P-cadherin and active domains thereof.

Devices

Bioactive agent eluting devices in accordance with embodiments herein can include those having an expandable portion. In some embodiments, the bioactive agent eluting device can include both an expandable portion and an non-expandable portion. An exemplary device is a balloon catheter. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523.

The present invention may be better understood with reference to the following examples. These examples are intended to be representative of specific embodiments of the invention, and are not intended as limiting the scope of the invention.

EXAMPLES

Example 1: Formation of Bioactive Agent-Eluting Balloon Coating Composed of Hydrophilic Basecoat and Hydrophobic Amorphous Bioactive Agent (Paclitaxel) Topcoat A 3.5×15 mm balloon (P/N 50051-004) was obtained from Minnesota Medtec, Inc. The balloon was inflated with minimal pressure to present a smooth surface.

Poly[vinyl pyrrolidone$^{99\%}$-co-N-(3-(4-benzoylbenzamido)propyl) methacrylamide$^{1\%}$] was obtained (PVP-BBA-APMA). This reagent can be prepared as described in U.S. Pat. Nos. 4,973,493; 4,979,959; 5,002,582; 5,263,992; and 5,741,551.

N-Acetylated poly[acrylamide$^{93.6\%}$-co-sodium-2-acrylamido-2-methylpropanesulfonate$^{4.9\%}$-co-N-(3-(4-benzoylbenzamido)propyl)methacrylamide$^{0.9\%}$]-co-methoxy poly(ethylene glycol)$_{1000}$ monomethacrylate$^{0.6\%}$ (percentages are mole percents) was obtained (PA-BBA-APMA-PEG). This reagent can be prepared as described in U.S. Pat. Nos. 4,979,959; 5,263,992; and 5,512,329.

Disodium 4,5-bis[(4-benzoylbenzyl)oxy]-1,3-benzenedisulfonate (DBDS) was obtained. This reagent can be prepared by combining 4,5-Dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360).

Poly[acrylamide$^{96.5\%}$-co-N-(3-(4-benzoylbenzamido)propyl)methacrylamide$^{3.5\%}$] was obtained (PA-BBA-APMA). This reagent can be prepared as described in U.S. Pat. Nos. 4,722,906; 4,973,493; 4,979,959; 5,002,582; 5,263,992; and 5,512,329.

A first basecoat coating solution (PVP-polyvinylpyrrolidone) was prepared. The solution consisted of PVP-BBA-APMA at 25 mg/ml, PA-BBA-APMA-PEG at 5 mg/ml, polyvinylpyrrolidone (PVP-K90) at 10 mg/ml, and DBDS at 0.25 mg/ml in a solvent of 85% water/15% isopropyl alcohol (v/v). As such, this first basecoat solution included predominantly polyvinylpyrrolidone as a hydrophilic polymer (though some PA was present).

A second basecoat coating solution (PA-polyacrylamide) was prepared. The solution consisted of PA-BBA-APMA at 10 mg/ml and DBDS at 0.5 mg/ml in a solvent of 50% water/50% isopropyl alcohol (v/v). As such, this second basecoat solution included predominantly polyacrylamide as a hydrophilic polymer.

A third basecoat coating solution (PA(2)-polyacrylamide) was prepared. The solution consisted of PA-BBA-APMA at 10 mg/ml in a solvent of 50% water/50% isopropyl alcohol (v/v). As such, this third basecoat solution included predominantly polyacrylamide as a hydrophilic polymer.

The basecoat solution was applied to the balloon using a dip coat method. Specifically, the balloon was immersed in the base coat coating solution with no dwell time. The balloon was then extracted from the solution at a speed of 0.5 cm/s. The basecoat was then air dried for at least 10 minutes. The base coat was then UV cured. Specifically the coated balloon was rotated in front of a Dymax 2000-EC series UV flood lamp with a 400 Watt metal halide bulb for 3 minutes, approximately 20 cm from the light source. Some balloons were left uncoated with a basecoat as a control.

A first topcoat solution was prepared by dissolving paclitaxel at a concentration of about 30-50 mg/ml in a solvent of ethyl acetate. A second topcoat solution was prepared by dissolving paclitaxel at a concentration of about 30-50 mg/ml in a solvent of chloroform.

The topcoat was applied by drop coating. Specifically, a positive displacement pipette was used to apply an appropriate volume of topcoat solution direct to the balloon to achieve a target drug load of 3 µg/mm$^2$. The balloon was then rotated by hand to evenly distribute topcoat solution over the balloon surface. The paclitaxel was deposited in a form that was amorphous.

Example 2: Bioactive Agent Transfer from Balloon to Simulated Vessel Wall (Silicone Tubing)

Silicone tubing (0.125 inch I.D., 0.188 inch O.D., 0.0315 inch wall) was obtained from Cole-Parmer Instrument Co. The silicone tubing was cut into 1.5 inch lengths.

The silicone tubing pieces were placed individually in 4 mL amber glass vial filled with 4 mL of PBS (phosphate buffer saline) pH-7.4, which was preheated in a water bath to 37° C.

A deflated, folded balloon (prepared as described above) was placed in a preheated (37° C.) 8 mL vial filled with 8 mL of PBS (phosphate buffer saline) pH-7.4 and soaked for 4 minutes. The balloon was slid into the inner lumen of the silicone tube (submerged inside 4 mL vial) and expanded for 30 seconds at 4 atmospheres air pressure. Balloon pressure was released and the balloon was removed from the tubing.

Figure 3:
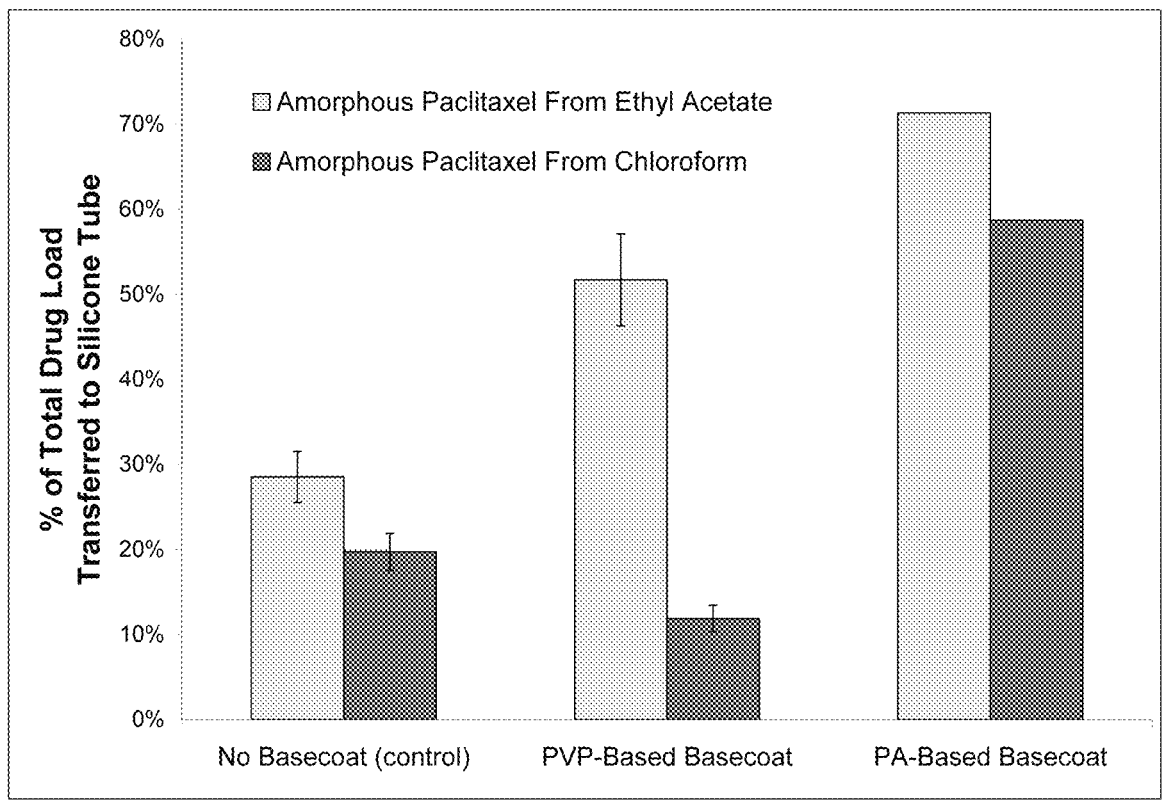
FIG. 3 is a graph showing bioactive agent transfer from a balloon to a silicon tube (simulated vessel).

The amount of paclitaxel transferred to the wall of the inner lumen of the tubing was then determined. Specifically, the tubing was submerged in 4 mL of a mixture (extraction media) of 0.1% glacial acetic acid in methanol for 24 hours. A 350 μL aliquot of the extraction media was transferred to a 96 well plate for bioactive agent content measurement by UV (232 nm). The results are shown in FIG. 3. The category of PA-based basecoat shown in FIG. 3 is inclusive of results obtained with both the second basecoat and the third basecoat coating solutions.

This example shows that a basecoat composed primarily of polyvinylpyrrolidone (PVP) or polyacrylamide (PA) increased the transfer of amorphous paclitaxel applied out of ethyl acetate to a simulated vessel by 81% and 150%, respectively, over a control balloon with no basecoat. This example further shows that a basecoat composed primarily of polyacrylamide (PA) increased the transfer of amorphous paclitaxel applied out of chloroform to a simulated vessel by 106% over a control balloon with no basecoat. Thus, this example shows that hydrophilic basecoats can be used to greatly increase the amount of a substantially amorphous hydrophobic bioactive agent delivered from a balloon device.

Finally, this example shows that a basecoat composed primarily of polyvinylpyrrolidone (PVP) decreased the transfer of amorphous paclitaxel applied out of chloroform to a simulated vessel by 58% over a control balloon with no base coat. While not intending to be bound by theory, it is believed that this decrease was because chloroform (from the bioactive agent composition) serves as an effective solvent to PVP and the PVP base coat formed an interpenetrating network with the paclitaxel in chloroform solution during the process of applying the bioactive agent top coat.

Example 3: Bioactive Agent Transfer from Balloon to Ex-Vivo Porcine Artery

Porcine artery was obtained from Pel-Freeze. The porcine artery was cut into 1.5 inch lengths.

The porcine artery pieces were placed individually in 4 mL amber glass vial filled with 4 mL of PBS (phosphate buffer saline) pH-7.4, which was preheated in a water bath to 37° C.

A deflated, folded balloon (prepared as described above) was placed in a preheated (37° C.) 8 mL vial filled with 8 mL of PBS (phosphate buffer saline) pH-7.4 and soaked for 4 minutes. The balloon was slid into the inner lumen of the porcine artery (submerged inside 4 mL vial) and expanded for 30 seconds at 4 atmospheres air pressure. Balloon pressure was released and the balloon was removed from the tubing.

Figure 4:
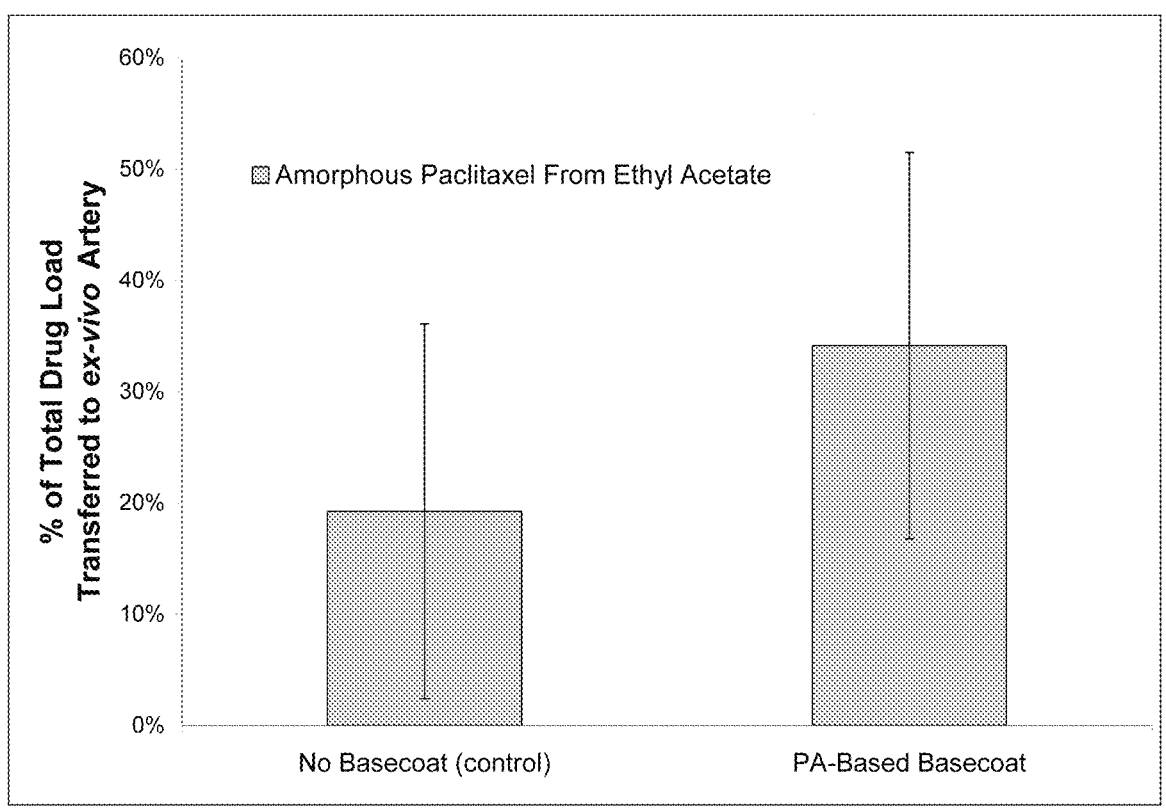
FIG. 4 is a graph showing bioactive agent transfer from a balloon to an ex vivo porcine vessel.

The amount of paclitaxel transferred to the wall of the inner lumen of the artery was then determined. Specifically, the artery was submerged in 4 mL of a mixture of 0.1% glacial acetic acid in methanol for 24 hours. The amount of paclitaxel in the extraction media was then determined via HPLC. The results are shown in FIG. 4. The category of PA-based basecoat shown in FIG. 4 is inclusive of results obtained with both the second basecoat and the third basecoat coating solutions.

This example shows that a basecoat composed primarily of polyacrylamide (PA) increases the transfer of amorphous paclitaxel applied out of ethyl acetate to a simulated vessel by 77%. Thus, this example shows that hydrophilic basecoats can be used to greatly increase the amount of a substantially amorphous hydrophobic bioactive agent delivered from a balloon device.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference. Nothing herein is to be construed as an admission that the inventors are not entitled to antedate any publication and/or patent, including any publication and/or patent cited herein.

The invention has been described with reference to various specific and preferred embodiments and techniques. However, it should be understood that many variations and modifications may be made while remaining within the spirit and scope of the invention.

Further Embodiments

In an embodiment, the invention includes a bioactive agent delivery device including a substrate, a hydrophilic polymer disposed on the substrate, and a substantially amorphous bioactive agent disposed on the surface of the hydrophilic polymer. In an embodiment, the hydrophilic polymer is covalently bonded to the substrate. In an embodiment, the hydrophilic polymer is covalently bonded to the substrate through the reaction product of a latent photoreactive group. In an embodiment, the substrate includes a polymer. In an embodiment, the polymer includes an elastomer. In an embodiment, the amorphous bioactive agent includes a hydrophobic bioactive agent. In an embodiment, the amorphous bioactive agent includes paclitaxel. In an embodiment, the amorphous bioactive agent comprises rapamycin. In an embodiment, the hydrophilic polymer selected from the group consisting of poly(acrylamide), poly(methacrylamide), poly(vinylpyrrolidone), poly(acrylic acid), poly(ethylene glycol), poly(vinyl alcohol), poly(HEMA), methyl vinyl ether/maleic anhydride copolymers, and vinyl pyrrolidone/(meth)acrylamide copolymers. In an embodiment, the hydrophilic polymer is poly(acrylamide). In an embodiment, the hydrophilic polymer is poly(vinylpyrrolidone).

In an embodiment, the invention includes a method of making a bioactive agent delivery device. The method includes depositing a hydrophilic polymer on a substrate forming a hydrophilic surface and depositing a substantially amorphous bioactive agent on the hydrophilic surface. In an embodiment, depositing the hydrophilic polymer on the substrate includes depositing a photo-polymer on the substrate, the photo-polymer comprising latent photoreactive groups and a hydrophilic backbone; and applying actinic radiation to the photo-polymer. In an embodiment, depositing a substantially amorphous bioactive agent on the hydrophilic surface includes mixing the amorphous bioactive agent with a solvent to form an bioactive agent mixture, depositing the bioactive agent mixture on the hydrophilic surface, and evaporating the solvent. In an embodiment, evaporation is carried out in a manner to preserve the amorphous characteristics of the bioactive agent. In an embodiment, the solvent for the bioactive agent mixture is selected such that it does not solvate the hydrophilic polymer. In an embodiment, the solvent includes ethyl acetate. In an embodiment, the amorphous bioactive agent includes a hydrophobic bioactive agent. In an embodiment, the amorphous bioactive agent includes paclitaxel. In an embodiment, the hydrophilic polymer is selected from the group consisting of poly(acrylamide), poly(methacrylamide), poly(vinylpyrrolidone), poly(acrylic acid), poly(ethylene glycol), poly(vinyl alcohol), poly(HEMA), methyl vinyl ether/maleic anhydride copolymers, and vinyl pyrrolidone/(meth)acrylamide copolymers.

In an embodiment, the invention includes a bioactive agent-eluting catheter including a catheter shaft; an expandable balloon disposed on the catheter shaft; a hydrophilic polymer disposed on the outside surface of the balloon; and a substantially amorphous bioactive agent disposed on the surface of the hydrophilic polymer. In an embodiment, the hydrophilic polymer is covalently bonded to the substrate. In an embodiment, the hydrophilic polymer is covalently bonded to the substrate through the reaction product of a latent photoreactive group. In an embodiment, the substrate includes a polymer. In an embodiment, the polymer is an elastomer. In an embodiment, the amorphous bioactive agent includes a hydrophobic bioactive agent. In an embodiment, the amorphous bioactive agent includes paclitaxel. In an embodiment, the amorphous bioactive agent includes rapamycin. In an embodiment, the hydrophilic polymer is selected from the group consisting of poly(acrylamide), poly(methacrylamide), poly(vinylpyrrolidone), poly(acrylic acid), poly(ethylene glycol), poly(vinyl alcohol), poly(HEMA), methyl vinyl ether/maleic anhydride copolymers, and vinyl pyrrolidone/(meth)acrylamide copolymers. In an embodiment, the hydrophilic polymer includes poly(acrylamide). In an embodiment, the hydrophilic polymer includes poly(vinylpyrrolidone).

The invention claimed is:

1. A bioactive agent delivery device comprising:
   an expandable substrate forming part of a balloon;
   a hydrophilic polymer layer disposed over the substrate, the hydrophilic polymer layer comprising a hydrophilic polymer comprising poly(ethylene glycol); and
   a hydrophobic bioactive agent composition layer disposed over the surface of the hydrophilic polymer layer, the hydrophobic bioactive composition layer comprising one or more forms of paclitaxel; and
   wherein the hydrophobic bioactive agent composition layer lacks the hydrophilic polymer.

2. The bioactive agent delivery device of claim 1, the bioactive agent composition comprising trace amounts of a solvent that does not solvate the hydrophilic polymer layer.

3. The bioactive agent delivery device of claim 1, further comprising a catheter shaft, wherein the expandable substrate forming part of the balloon is disposed on the catheter shaft.

4. The bioactive agent delivery device of claim 1, wherein the hydrophilic polymer layer is covalently bonded to the expandable substrate through the reaction product of a latent photoreactive group.

5. The bioactive agent delivery device of claim 1, the expandable substrate comprising an elastomeric material.

6. The bioactive agent delivery device of claim 1, the expandable substrate comprising a polyamide.

7. The bioactive agent delivery device of claim 1, wherein the thickness of the expandable substrate is from 5 µm to 100 µm.

8. The bioactive agent delivery device of claim 1, wherein the hydrophilic polymer layer is cross-linked through the reaction product of a latent photoreactive group.

9. The bioactive agent delivery device of claim 1, wherein the paclitaxel releases from the device into an aqueous environment in under 30 seconds when exposed to an aqueous environment.

10. The bioactive agent delivery device of claim 1, wherein the paclitaxel is present in the hydrophobic bioactive composition layer in crystalline and amorphous forms.

11. A bioactive agent-eluting catheter comprising:
    a catheter shaft;
    an expandable balloon disposed on the catheter shaft, the expandable balloon comprising an expandable substrate; and
    a hydrophilic polymer layer disposed over the substrate, the hydrophilic polymer layer comprising a hydrophilic polymer comprising poly(ethylene glycol);
    a hydrophobic bioactive agent composition layer disposed over the surface of the hydrophilic polymer layer, the hydrophobic bioactive composition layer comprising one or more forms of paclitaxel; and
    wherein the hydrophobic bioactive agent composition layer lacks the hydrophilic polymer.

12. The bioactive agent-eluting catheter of claim 11, wherein the paclitaxel is present in the hydrophobic bioactive composition layer in crystalline and amorphous forms.

13. The bioactive agent-eluting catheter of claim 11, wherein the paclitaxel releases from the device into an aqueous environment in under 30 seconds when exposed to an aqueous environment.

* * * * *